United States Patent
Kim et al.

(10) Patent No.: US 10,478,069 B2
(45) Date of Patent: Nov. 19, 2019

(54) METHOD FOR ESTIMATING TIME OF OCCURRENCE OF INFARCT ON BASIS OF BRAIN IMAGE

(71) Applicant: THE ASAN FOUNDATION, Seoul (KR)

(72) Inventors: Nam Kug Kim, Seoul (KR); Dong Wha Kang, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 227 days.

(21) Appl. No.: 15/557,423

(22) PCT Filed: Mar. 12, 2015

(86) PCT No.: PCT/KR2015/002420
§ 371 (c)(1),
(2) Date: Sep. 11, 2017

(87) PCT Pub. No.: WO2016/143927
PCT Pub. Date: Sep. 15, 2016

(65) Prior Publication Data
US 2018/0271373 A1    Sep. 27, 2018

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *G01R 33/5608* (2013.01); *G01R 33/56341* (2013.01); *G01R 33/56366* (2013.01); *G06T 7/0014* (2013.01); *G06T 7/30* (2017.01); *G06T 2207/10088* (2013.01); *G06T 2207/30016* (2013.01)

(58) Field of Classification Search
CPC ..................................................... A61B 5/0042
See application file for complete search history.

(56) References Cited

U.S. PATENT DOCUMENTS

| | | | |
|---|---|---|---|
| 2002/0161292 A1* | 10/2002 | Wintermark | A61B 5/0275 600/407 |
| 2004/0106864 A1* | 6/2004 | Rose | A61B 5/055 600/410 |

(Continued)

FOREIGN PATENT DOCUMENTS

| | | | |
|---|---|---|---|
| JP | 2000-126150 A | 5/2000 | ............ A61B 5/055 |
| JP | 2004-024637 A | 1/2004 | ............ A61B 5/055 |

OTHER PUBLICATIONS

Cho et al., "Safety and Efficacy of MRI-Based Thrombolysis in Unclear-Onset Stroke", Cerebrovascular Diseases 2008; 25, pp. 572-579 (Year: 2008).*

*Primary Examiner* — Nay A Maung
*Assistant Examiner* — Jose Torres
(74) *Attorney, Agent, or Firm* — Studebaker & Brackett PC

(57) ABSTRACT

Disclosed is a method for estimating an onset time of an infarct region based on brain images, the method including: obtaining brain images; extracting from the infarct region included in the brain images a set of quantitative values that vary according to the onset time of the infarct region; and having the set of quantitative values correspond to the onset time of the infarct region by applying a corresponding relation prepared therefor.

9 Claims, 18 Drawing Sheets

(51) Int. Cl.
  *G06T 7/30*    (2017.01)
  *G01R 33/56*   (2006.01)
  *G01R 33/563*  (2006.01)
  *G06T 7/00*    (2017.01)

(56) References Cited

U.S. PATENT DOCUMENTS

| | | | |
|---|---|---|---|
| 2008/0021502 A1 | 1/2008 | Imielinska et al. | 607/1 |
| 2009/0034812 A1* | 2/2009 | Nowinski | A61B 5/055 |
| | | | 382/131 |
| 2009/0080748 A1 | 3/2009 | Reeves et al. | 382/131 |
| 2010/0121846 A1* | 5/2010 | Habets | G06F 16/58 |
| | | | 707/728 |
| 2010/0231216 A1 | 9/2010 | Prakash K.N. et al. | 324/309 |
| 2016/0180042 A1* | 6/2016 | Menon | G16H 30/20 |
| | | | 705/2 |

* cited by examiner

Signal evolution on DWI and ADC map (a)

(b)

| num | Date of hospitalization | Thrombolysis (IV, IA, stent, etc) | Imaging Time (hr. after onset) | Double | 3mm |
|---|---|---|---|---|---|
| 1 | 5/19/2013 | o | 1:15 | | |
| 2 | 5/15/2013 | o | 2:06 | | |
| 3 | 2013/9/11 | o | 2:27 | o | |
| 4 | 2013/8/28 | o | 2:26 | | |
| 5 | 2013/9/25 | o | 2:14 | o | |
| 6 | 2013/9/18 | o | 0:37 | | |
| 7 | 2013/9/3 | o | 0:07 | | o |
| 8 | 6/19/2013 | o | 0:58 | | |
| 9 | 2013/9/10 | o | 2:23 | o | |
| 10 | 3/28/2013 | o | 5:27 | | |
| 11 | 4/7/2013 | o | 2:31 | | |
| 12 | 5/13/2013 | o | 0:27 | | |
| 13 | 5/15/2013 | o | 0:55 | | |
| 14 | 7/7/2013 | o | 1:46 | | |
| 15 | 2013/9/11 | o | 1:15 | o | |

(a) adc (b) flair (a) GRE

```
. reg var6 var1 var2 var3 var4 var5
```

| Source   | SS         | df | MS         |
|----------|------------|----|------------|
| Model    | 15179.5987 | 5  | 3035.91974 |
| Residual | 9769.63206 | 7  | 1395.66172 |
| Total    | 24949.2308 | 12 | 2079.10256 |

Number of obs = 13
F( 5, 7) = 2.18
Prob > F = 0.1697
R-squared = 0.6084
Adj R-squared = 0.3287
Root MSE = 37.359

| var6  | Coef.      | Std. Err. | t     | P>|t| | [95% Conf. | Interval] |
|-------|------------|-----------|-------|-------|------------|-----------|
| var1  | 1.736962   | .752878   | 2.31  | 0.054 | -.0433118  | 3.517235  |
| var2  | -1.783904  | 1.196123  | -1.49 | 0.179 | -4.612286  | 1.044478  |
| var3  | -.517677   | .2184859  | -2.37 | 0.050 | -1.034314  | -.0010398 |
| var4  | .0971691   | .4953873  | 0.20  | 0.850 | -1.074236  | 1.268574  |
| var5  | -.1983461  | .7226485  | -0.27 | 0.792 | -1.907138  | 1.510446  |
| _cons | 99.00903   | 183.631   | 0.54  | 0.606 | -335.2092  | 533.2272  |

(b) multi-regression

FIG. 12B

METHOD FOR ESTIMATING TIME OF OCCURRENCE OF INFARCT ON BASIS OF BRAIN IMAGE

CROSS-REFERENCE TO RELATED APPLICATIONS

This application is a national phase application of PCT Application No. PCT/KR2015/002420, filed on 12 Mar. 2015 The entire disclosure of the application identified in this paragraph is incorporated herein by reference.

FIELD

The present disclosure relates generally to a method for estimating an onset time of an infarct region based on brain images. More specifically, it relates to a method for estimating an onset time of an infarct region using a set of quantitative values extracted from brain images where the onset time of an infarct region is not known.

BACKGROUND ART

This section provides background information related to the present disclosure which is not necessarily prior art.

Medical imaging is broadly used for evaluating the condition of a lesion within a patient. For example, MRI brain images of a patient suffering from an acute stroke such as cerebral infarct or cerebral hemorrhage are taken to evaluate a lesion that is created.

Cho A H, Sohn S I, Han M K, et al. (Safety and Efficacy of MRI-based Thrombolysis in Unclear-Onset Stroke. A preliminary report. Cerebrovasc Dis 2008; 25: 572-579) described a method for estimating an onset time of an infarct region based on MRI FLAIR (fluid-attenuated inversion recovery) images of a patient whose onset time of cerebral infarct is not clear or specified. According to this article, PWI-DWI mismatch (positive perfusion-diffusion mismatch) conditions and FLAIR CHANGE (absence of well-developed fluid-attenuated inversion recovery changes of acute diffusion lesions) conditions are included in MRI-based conditions used as the grounds for estimating an onset time of a cerebral infarct.

However, such conditions including the PWI-DWI mismatch and the FLAIR CHANGE mentioned in the article are empirical indices of physicians that are heavily dependent on visual inspection such that they are less likely to provide quantitative and objective criteria for an accurate decision.

Shlee S. Song, Lawrence L. Latour, Carsten H. Ritter, et al. (A Pragmatic Approach Using Magnetic Resonance Imaging to Treat Ischemic Strokes of Unknown Onset Time in a Thrombolytic Trial. The American Heart Association online Jun. 12, 2012) described a method for estimating an onset time of a cerebral infarct by analyzing brightness (e.g., intensity) in a FLAIR image corresponding to diffusion-positive regions (SIR; Reader-measured signal intensity ratio).

This SIR method still shows limitations to present objective indices because it is rated or graded by a number of image readers to determine an SIR value. Moreover, the SIR method has a limited reliability as it uses one single parameter, i.e., the intensity of a FLAIR image, to determine an onset time of cerebral infarct. Considering that an infarct region has different levels of intensity in the FLAIR image at different times, depending on certain factors, such as, an infarct location, an infarct volume, the age and gender of a patient and so on, subjects show greatly varying levels of intensity. In addition, designating an onset time from a specific SIR value, irrespective of the fact that those time-dependent intensities in the FLAIR image show a spectrum distribution, makes the SIR method less objective as well as less reliable.

DISCLOSURE

Technical Problem

The problems to be solved by the present disclosure will be described in the latter part of the best mode for carrying out the invention.

Technical Solution

This section provides a general summary of the present disclosure and is not a comprehensive disclosure of its full scope or all of its features.

According to one aspect of the present disclosure, there is provided a method for estimating an onset time of an infarct region based on brain images, the method including: obtaining brain images; extracting from the infarct region included in the brain images a set of quantitative values that vary according to the onset time of the infarct region; and having the set of quantitative values correspond to the onset time of the infarct region by applying a corresponding relation prepared therefor.

Advantageous Effects

The advantageous effects of the present disclosure will be described in the latter part of the best mode for carrying out the invention.

BRIEF DESCRIPTION OF THE DRAWINGS

FIG. 9 illustrates an exemplary data sheet obtained from patients.

FIGS. 12A and 12B illustrates an exemplary method of robust regression to find the relationship between a set of quantitative values acquired from GRE images and an onset time of an infarct region, and an exemplary method of multi-regression to find the relationship between a set of quantitative values and an onset time of an infarct region.

DETAILED DESCRIPTION

Hereinafter, the present disclosure will now be described in detail with reference to the accompanying drawings. The following description is presented for purposes of illustration only and not of limitation as the scope of the invention is defined by the appended claims. For example, the steps mentioned in any of the method or process may be executed in any order and are not necessarily limited to the order provided. Also, any reference to singular includes plural embodiments, and vice versa.

Figure 1:
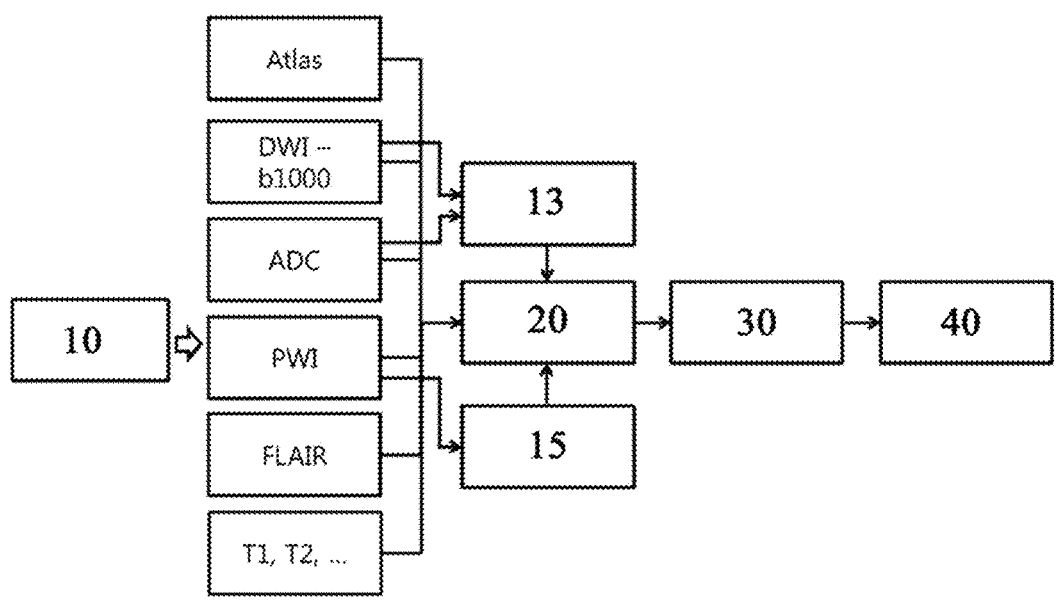
FIG. 1 illustrates an exemplary embodiment of a method for estimating an onset time of an infarct region based on brain images according to the present disclosure.

FIG. 1 illustrates an exemplary embodiment of a method for estimating an onset time of an infarct region based on brain images according to the present disclosure.

In the method, brain images are first obtained (10). These obtained brain images (e.g. DWI, ADC, PWI, FLAIR, T1, T2, etc.) includes an infarct region. A set of quantitative values, which vary according to an onset time of an infarct region, is extracted (30). With the application of a corresponding relation prepared for having the set of quantitative values correspond to an onset time of the infarct region, the set of quantitative values is then matched to the onset time of the infarct region (40).

After the brain images are obtained, and before the set of quantitative values is extracted, the infarct region may be segmented using at least one of the brain images that were obtained (13). A penumbra of the infarct region may be segmented using at least one of the brain images that were obtained (15). Moreover, these brain images including at least one brain image with a segmented penumbra or infarct region may be registered (20).

The set of quantitative values includes at least one information about size, location and intensity of the penumbra or infarct region from those registered brain images.

Figure 2:
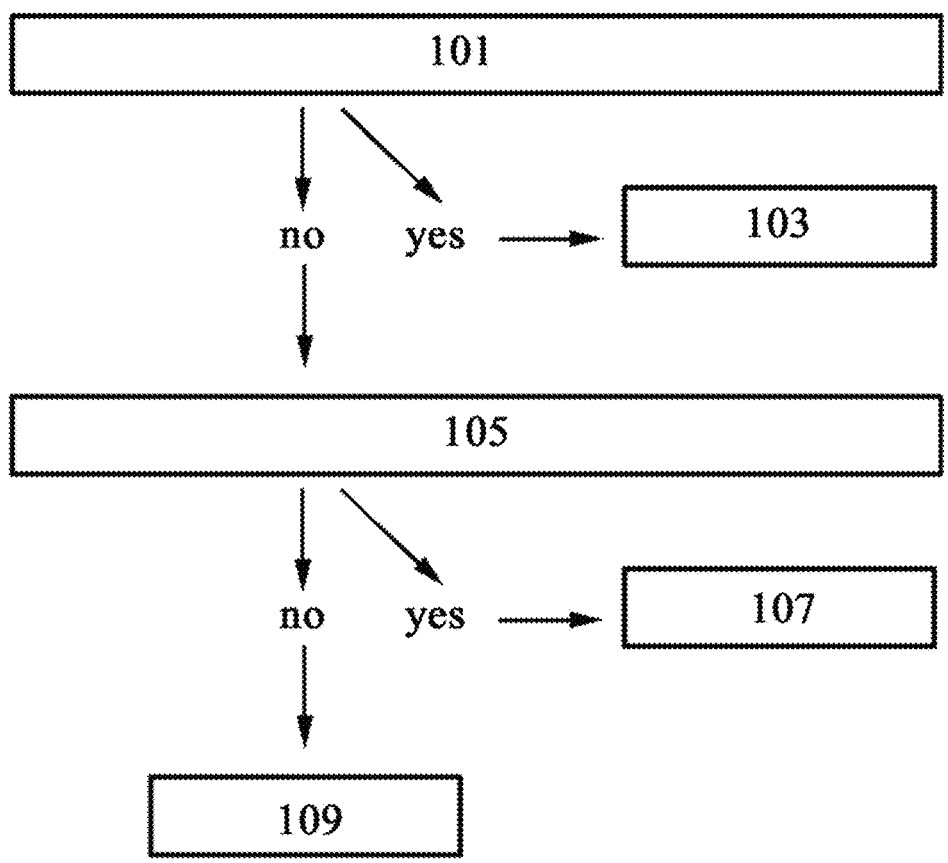
FIG. 2 illustrates an exemplary method for distinguishing a case where an onset time of an infarct region is clear from a case where an onset time of an infarct region is not clear.

FIG. 2 illustrates an exemplary method for distinguishing a case where an onset time of an infarct region is clear from a case where an onset time of an infarct region is not clear.

The disclosed method for estimating an onset time of an infarct region based on brain images according to this example is equally applicable to a case where an onset time of an infarct region is specified and to a case where an onset time of an infarct region is not specified. The estimation of an onset time is carried out using a corresponding relation that has been prepared in advance. The corresponding relation can be prepared by a classifier which classifies a set of quantitative values by onset time of an infarct region.

For instance, the corresponding relation can be prepared using a classifier to have a set of accumulated quantitative values acquired from brain images whose onset times of an infarct region are known correspond to an onset time of an infarct region of interest, with the classifier incorporating at least one of the following: uni-variate regression, multi-variate regression, robust regression, support vector regression, a decision tree, a Bayesian classifier and curve fitting.

As aforementioned, FIG. 2 describes an example of how to determine a case where an onset time of an infarct region is specified (Clear Onset Time), and a case where an onset time of an infarct region is not specified (Unclear Onset Time).

Suppose that an acute stroke has occurred in the brain, for example. In this case, Last-known normal time and First-found abnormal time are checked to see if they coincide (101). If 'Yes', i.e. the last-known normal time and the first-found abnormal time coincide, it is classified as a clear onset (103). If 'No', i.e. the last-known normal time and the first-found abnormal time do not coincide, it is checked if a patient arrived at the emergency room (ER) within 4.5 hours since the last-known normal time (105). If 'Yes', i.e. the patient arrived at the emergency room within 4.5 hours, the patient might be subjected to thrombolytic therapy although this is an unclear onset case (107). If 'No', i.e. the patient arrived at the emergency room after 4.5 hours, this is an unclear onset case and the patient is not subjected to thrombolytic therapy (109).

It should be noted that the method for estimating an onset time of an infarct region based on brain images according to the present disclosure is not intended to select a treatment regimen or make a diagnosis (e.g., whether the thrombolytic therapy is necessary), but simply to estimate an onset time of an infarct region.

According to the disclosed method for estimating an onset time of an infarct region based on brain images, the onset time of an infarct region is estimated based on a set of quantitative values extracted from brain images. In other words, the method for estimating an onset time of an infarct region based on brain images disclosed herein does not depend on any uncertain factors such as time elapsed since the Last-known normal time.

For instance, the corresponding relation is prepared by a classifier that is trained or taught to have a set of quantitative values correspond to an onset time of an infarct region.

The following will describe in further details each process of the method for estimating an onset time of an infarct region based on brain images.

Figure 3:
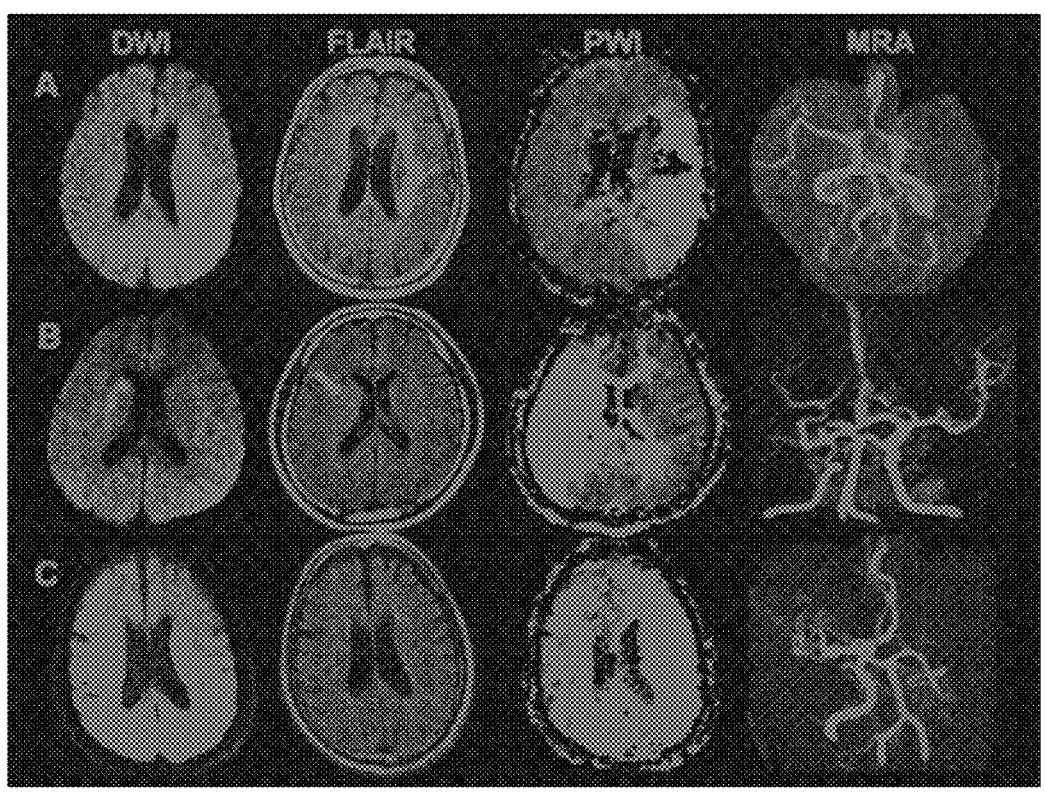
FIG. 3 illustrates brain images by MRI.

FIG. 3 illustrates brain images by MRI.

Firstly, brain images are obtained (10 in FIG. 1).

For instance, MRI images of the brain are generated. These brain images include DWI images, ADC images, PWI images, FLAIR images, T1 images, T2 images, GRE images and the like. The brain images in this exemplary embodiment are not limited to MRI images, but may include CT images or other medical images.

The brain images are generated using pulse sequences that are combined when needed for each image. Therefore, the brain images may have different modalities. Among others, ADC images are obtained through a calculation process of DWI images.

In order to obtain images by MRI, a large number of RF pulses should be applied. RF pulses having the same magnitude are applied at regular time intervals called TR (repetition time). There is delay time or echo time called TE (time to echo). Since a signal cannot be measured immediately after RF pulses are applied, a short space of time should pass, and a signal is not measured until a designated amount of time has passed. TE corresponds to this short space of time.

TR and TE can be modified by an examiner. Suitably modified TR and TE allow to obtain T1 or T2 images that can be applied clinically.

The following will briefly describe brain images from which a set of quantitative values can be extracted.

DWI (diffusion weighted imaging) is an imaging technique that allows the mapping of the diffusion motion of molecules, specifically water molecules, in biological tissues (see FIG. 3). The diffusion of water molecules in the tissue is not free. DWI represents collision of water molecules with fibrous tissues or cellular membranes. Thus, the diffusion pattern of water molecules show the normality or abnormality of tissues. In particular, DWI can show the fiber structure of brain white matter, or the normality or abnormality of brain gray matter.

ADC (apparent diffusion coefficient) is a diffusion coefficient as a function of temperature. ADC can be calculated with DWI as cell walls exist in the body and the temperature of body is not uniform throughout. DWI images and ADC images are inverse images. In an infarct region, water amount outside the cell is reduced because of cell expansion. Such a region having reduced diffusion becomes a region of a lower decrease in signal strength when taken by DWI, while it turns out bright in a DWI image. Meanwhile, this region having reduced diffusion turns out darker in an ADC image than normal. A water like liquid such as CSF (cerebrospinal fluid) is a free diffusion region such that it turns out bright in the ADC image and dark in the DWI image.

PWI (perfusion weighted imaging) is an imaging technique which is able to show the perfusion of tissues by blood (see FIG. 3). For instance, with gadolinium as a contrast agent, it is possible to acquire parameters such as blood flow, blood flow velocity, MTT (main transit time) and TTP (time to peak) from an MRI image.

FLAIR image is an image where a signal from fluids is nulled (see FIG. 3). For instance, it can be used in MRI of the brain to suppress CSF effects on the image. The FLAIR image well brings out the anatomy of the brain. A signal from a certain tissue can be suppressed by selecting an appropriate inversion time according to tissue.

T1 and T2 images are those images having emphasized T1 or T2 effects of a certain tissue through the adjustment of TR and TE. When the applied RF (radio frequency) pulses are blocked during an MRI process, protons in the tissue release their absorbed energy to the peripheral tissues and are realigned in the direction of an external magnetic field BO (Z-axis direction). T1 denotes realignment time of proton spins along the vertical axis (i.e. Z-axis direction). In other words, it is a time constant of a curve with restored magnetization in the Z-axis direction. T1, which is a time constant of restoring magnetization, is often called vertical-axis relaxation time or spin-lattice relaxation time. When RF pulses are blocked, however, X- and Y-components of the magnetization decay. T2 is a time constant of a decay curve of these X- and Y-components of the magnetization. It is often called a transverse relaxation time or spin-spin relaxation time. T1 and T2 are unique values of a tissue, and they vary among water, solids, fats and proteins. When TR is increased, T1 effect is diminished. On the other hand, when TR is decreased, T1 effect (contrast) gets stronger, that is, a T1 emphasized image is obtained. When TE is decreased, T2 effect is diminished. On the other hand, when TE is increased, T2 effect gets stronger, that is, a T2 emphasized image is obtained.

The MRA image herein shows an MRI image of blood flow taken using a contrast agent.

A qualitative analysis can be carried out on the brain images described above.

For instance, mismatches of DWI-PWI are visually inspected to evaluate the mismatch levels of infarct and penumbra regions affected by the infarct region. Alternatively, a state where a white region appeared on the DWI image but no white region has not yet appeared on the FLAIR image (FLAIR negative) can be designated as an early stage of a cerebral infarct where the onset time of the cerebral infarct is not long ago.

However, such a qualitative decision has a low level of accuracy and reliability. Unlike those methods based on this qualitative decision, the method for estimating an onset time of an infarct region according to the present disclosure is characterized by extracting a set of quantitative values from brain images and then estimating the onset time based on the set of quantitative values.

Returning to FIG. 1, once brain images are obtained, an infarct region in at least one of the obtained brain images can be segmented (13). Moreover, a penumbra region of the infarct region in the at least one of the brain images can be segmented (15). The penumbra region denotes a region located at the periphery of the infarct region or a region surrounding the infarct region. Under the influence of an infarct, the penumbra region experiences blood supply disorders.

For instance, an infarct in the early stage is well visible in a DWI image. Hence, an infarct region can be segmented using the DWI or ADC image (13). Meanwhile, a penumbra region or penumbra of the infarct is well visible in a PWI image. Hence, the penumbra region can be segmented using the PWI image (15).

Next, the brain images including at least one brain image with such a segmented infarct or penumbra region are registered (20). For instance, anatomical FLAIR or T1 and T2 images, a DWI or ADC image with a segmented infarct region, a PWI image and the other brain images are registered. Together with them, Brain CT images may also be registered. While this exemplary embodiment registers a number of brain images, it is not absolutely necessary to register all of the brain images described above. Depending on a purpose of viewing brain images, two or more brain images, preferably two or more brain images having different modalities are registered.

In this exemplary embodiment, the rest brain images are registered with respect to the DWI image with a segmented infarct region. This can be performed by rigid registration. Alternatively, non-rigid registration can also be performed although the brain, unlike the heart or the lung, does not move or hardly moves.

A template image of the brain can be used as the basis of registration (see 25 in FIG. 1). As such, template information is incorporated into those brain images described above (e.g., DWI, PWI, FLAIR images). It is important to know the size of an infarct or penumbra region, but it is more important to know where in the brain the infarct has occurred. This information can be generated using the template image. In general, a template image is an image of a standard brain, which is segmented (split) based on atlas information. For instance, a brain image basically includes Hyper-Campus, amygdala, thalamus, white matter and gray matter regions. This atlas map (template image) may be used as there is very little difference, if any, among people.

A set of quantitative values is then extracted from the infarct region of the registered brain images (30). For instance, a set of quantitative values indicates information on an infarct region related to an onset time thereof. Preferably, a set of quantitative values that vary according to an onset time of an infarct region is extracted from the registered brain images. The set of quantitative values can include at least one selected from the group consisting of information on the intensity, size and location of an infarct region.

For instance, two or more quantitative values, including an infarct volume $V_I$, an infarct location $V_{IL}$, a penumbra volume $V_P$, a penumbra position $V_{PL}$, mismatch M between an infarct region and a penumbra region, an average intensity of the infarct region in each brain image (e.g., $DI_{DWI}$, $DI_{ADC}$, $DI_{FLAIR}$, $DI_{T1}$, $DI_{T2}$), and an average intensity of the penumbra region in each brain image (e.g., $DP_{DWI}$, $DP_{ADC}$, $DP_{FLAIR}$, $DP_{T1}$, $DP_{T2}$), can be acquired from the registered brain images. Information on intensity is preferably included because it is believed that the average intensity of an infarct region in each brain image (e.g., $DI_{DWI}$, $DI_{ADC}$, $DI_{FLAIR}$, $DI_{T1}$, $DI_{T2}$) is closely related to an onset time of the infarct region.

For instance, if an infarct mask with a segmented infarct region is overlaid on the template image of the brain described above, one can find out how large an infarct is and where an infarct has occurred in the brain. In one example, if a brain template and a brain image of a patient are registered, one can find out from the patient's brain image the size of a segmented infarct region and in which site of the brain the segmented infarct region is located. Similarly, if a brain template and a PWI image with a segmented penumbra are registered, one can find out the size of the penumbra and in which site of the brain the penumbra is located. This overlaying operation also makes it possible to acquire DWI-PWI mismatch information. Besides, if a FLAIR image is overlaid together, it is possible to acquire not only further information on the structure of the brain, but also any pre-existing damage or problem in the infarct or penumbra region before the infarction has occurred.

Figure 4:
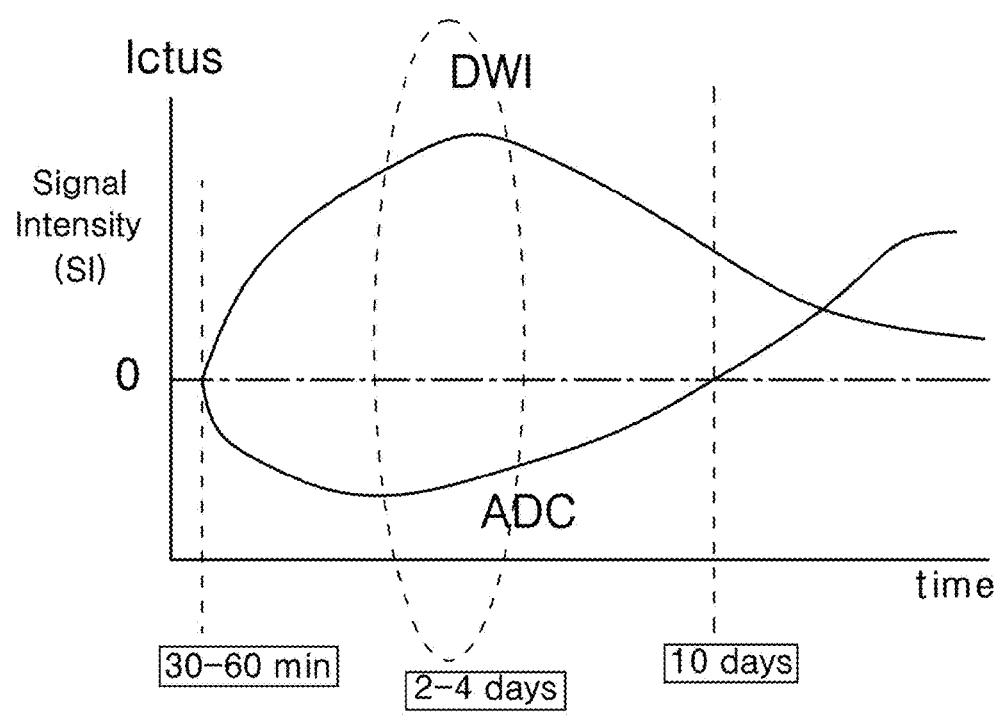
FIG. 4 illustrates a change in intensity levels of an infarct region in a DWI image according to an onset time of the infarct region.

FIG. 4 illustrates a change in intensity levels of an infarct region in a DWI image according to an onset time of the infarct region, and the intensity of an ADC image is shown as an inversed intensity of the DWI image. In other words, FIG. 4 shows a method for roughly estimating an onset time of a cerebral infarct using a single parameter. As discussed previously, however, any method using a single parameter has a low level of accuracy and reliability. Considering that an infarct region has different levels of intensity in the DWI image at different times, depending on certain factors, such as, an infarct location, an infarct volume, the age and gender of a patient, and so on, subjects show greatly varying levels of intensity. Moreover, it is regarded inappropriate to designate an onset time from a specific DWI intensity value, irrespective of the fact that those time-dependent intensities in the DWI image show a spectrum distribution.

Figure 5:
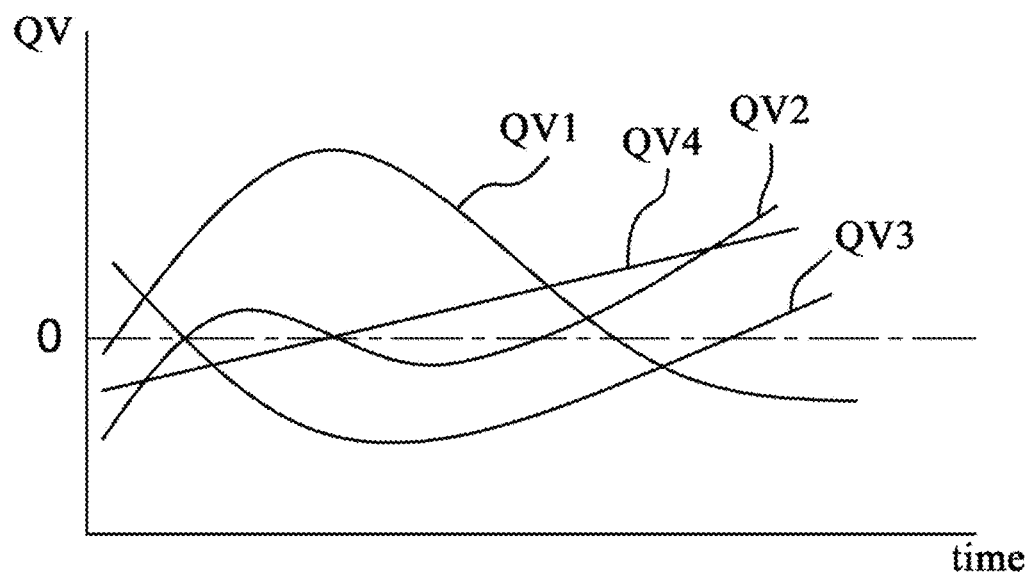
FIG. 5 illustrates a pattern of variable quantitative values extracted from brain images as a function of time.

FIG. 5 illustrates a pattern of variable quantitative values extracted from brain images as a function of time. In this exemplary embodiment, multiple parameters are used to more accurately and more reasonably estimate an onset time of an infarct region based on brain images. MRI can generate a variety of images suitable for clinical purposes through diverse combination of pulse sequences as well as proper combination of TR and TE, as described previously.

FIG. 5 shows how different quantitative parameters (QV1, QV2, QV3, QV4) from those diverse brain images vary by time. For convenience of description, the pattern of these variable quantitative parameters (QV1, QV2, QV3, QV4) in FIG. 5 is shown in a probable pattern, and it does not represent actual measurement results. In FIG. 5, QV1 is approximately similar to the DWI pattern, and QV3 is similar to the ACD pattern. Other patterns similar to or different from those shown in FIG. 5 can be obtained from accumulated data on the aforementioned quantitative values ($V_I$, $V_{IL}V_P$, $V_{PL}$, M, $DI_{DWI}$, $DI_{ADC}$, $DI_{FLAIR}$, $DI_{T1}$, $DI_{T2}$, $DP_{DWI}$, $DP_{ADC}$, $DP_{FLAIR}$, $DP_{T1}$, $DP_{T2}$ and so on). In other words, it is possible to obtain quantitative values that vary according to an onset time of an infarct region.

For instance, multi-modality brain images can be obtained from patients whose onset time of an infarct region has been known (clear onset). Then sets of quantitative values from these multi-modality brain images can be accumulated. Further, through an animal experiment, it is also possible to accumulate a set of quantitative values that vary by time from an onset time of an infarct in the same subject.

By plotting a graph as shown in FIG. 5 from such accumulated data on a set of onset time-quantitative values, a desired onset time can be determined from any quantitative value, or if not, roughly specified through a combination with other quantitative values.

For instance, using a quantitative value QV1, it is possible to estimate the onset time of an infarct region to be approximately in a zone between a first onset time and a second onset time. Likewise, using a quantitative value QV4, it is possible to estimate the onset time of an infarct region to be approximately in a zone between a third onset time and a fourth onset time. As such, a number of quantitative values (multiple parameters) are employed to estimate onset time zones of an infarct region. An intersection of these estimated onset time zones of an infarct region would provide a more accurate result on the onset time.

Figure 6A:
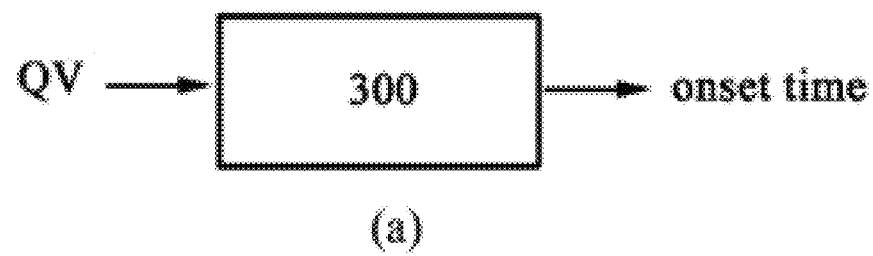
FIG. 6 illustrates an exemplary method for generating a corresponding relation.
Figure 6B:
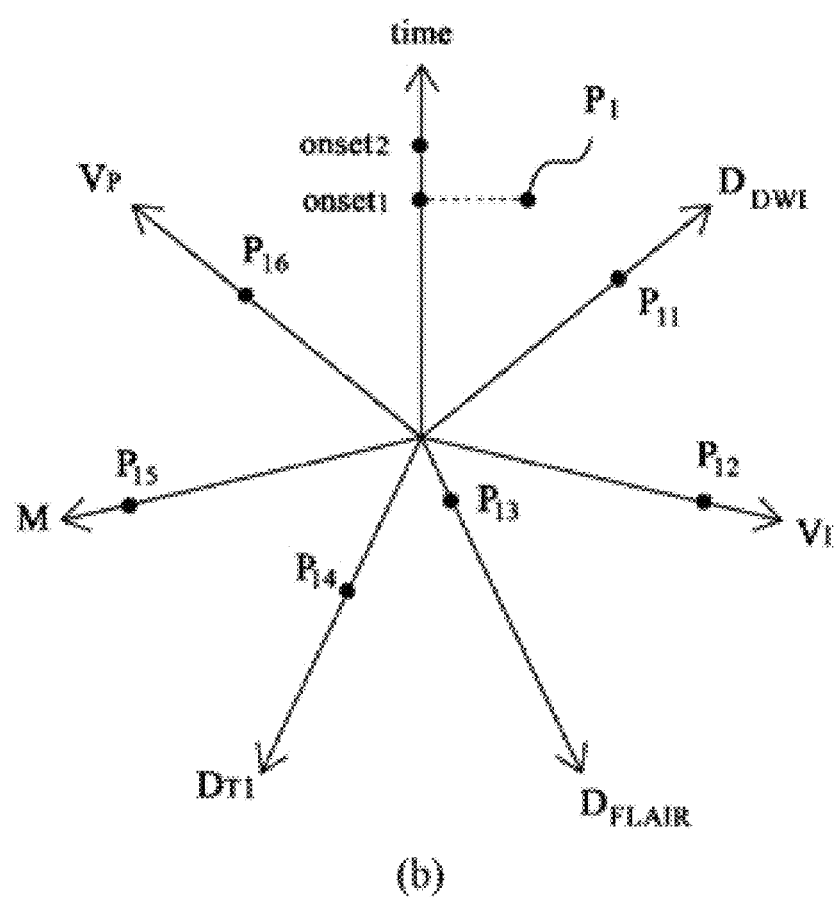

FIG. 6 illustrates an exemplary method for generating a corresponding relation, in which FIG. 6a shows that an extracted set of quantitative values QV corresponds to an onset time by a corresponding relation 300, and FIG. 6b shows an exemplary relationship between a set of quantitative values QV and onset times of an infarct region.

This exemplary method is a more generalized version of the method shown in FIG. 5 for specifying an onset time using multiple parameters, and employs a corresponding relation to have a set of quantitative values correspond to time of an infarct region (e.g., an onset time of an infarct region, or time relevant to the progress of an infarct region). The corresponding relation is prepared using a classifier 300 that is trained or taught to have a set of accumulated quantitative values correspond to an onset time of an infarct region of interest. Examples of the classifier 300 incorporates may include statistical schemes such as uni-variate regression or multi-variate regression, robust regression, support vector regression, a decision tree, and a Bayesian classifier. Alternatively, the corresponding relation can also be prepared by curve fitting a relation between a set of quantitative values and onset times.

The corresponding relation can have a higher level of accuracy and reliability through training and learning for corresponding a set of quantitative values to an onset time of an infarct region, using the accumulated data on onset time—a set of quantitative values. Here, training and learning indicate revising and complementing or amending a corresponding relation using accumulated data on onset time—a set of quantitative values. For instance, the level of accuracy of estimation of an onset time by a corresponding relation can be evaluated after repeatedly corresponding a set of quantitative values extracted from brain images where an onset time of an infarct region is not known to an onset time of an infarct region. In addition, the level of validity of estimation of an onset time by a corresponding relation can be evaluated after corresponding a set of quantitative values extracted from brain images where an onset time of an infarct region is known to an onset time of an infarct region.

As shown in FIG. 6b, the corresponding relation can be understood as points (P1: P11, P12, P13, P14, P15, P16, oneset1) in a multi-dimensional space where a set of quantitative values (P11, P12, P13, P14, P15, P16; e.g., $DI_{DWI}$, $V_I$, $DI_{FLAIR}$, $DI_{T1}$, M, $V_P$) corresponds to an onset time onset1. This corresponding relation can be prepared for multiple time points including an onset time onset2.

Various sets of quantitative values can be generated by combining a number of different quantitative values. While it is possible to use all of the quantitative values available together, it is preferable to select certain quantitative values that can operate the classifier at optimum performance levels. In other words, optimal features may be selected by SFS (sequential forward selection) scheme as it takes long to check operations of the classifier on an entire set of quantitative values. Therefore, by way of example, one quantitative value can be input to an empty set of quantitative values, and then only those quantitative values of an increasing accuracy may be selected. Inputting a selected set of quantitative values to the classifier to classify an onset time of an infarct region is illustrated in FIG. 6a. Performing a multi-dimensional classification using a set of many different quantitative values is illustrated in FIG. 6b.

Figure 7:
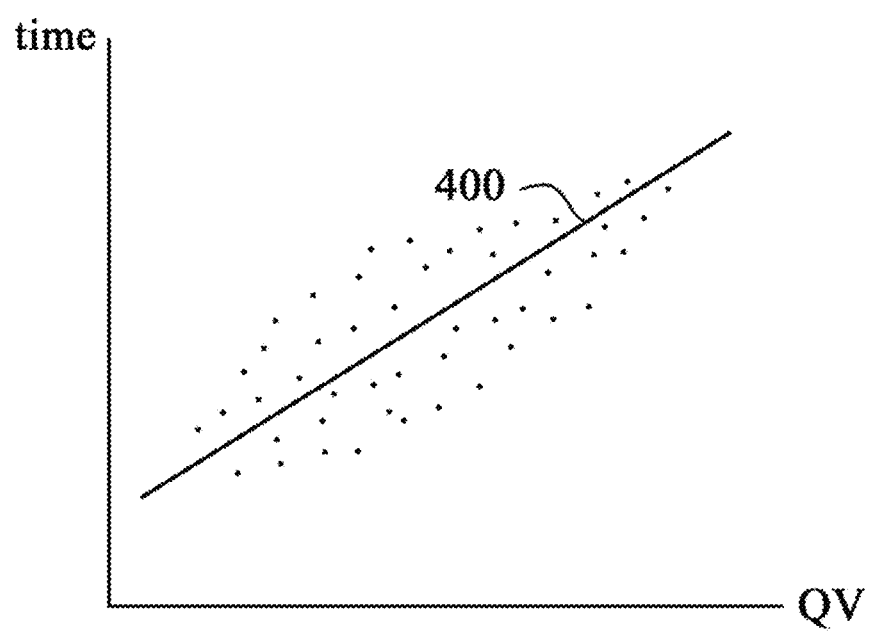
FIG. 7 illustrates an exemplary corresponding relation generated by regression analysis.

FIG. 7 illustrates an exemplary corresponding relation generated by regression analysis. Here, a classifier is used and multi-variate regression can be conducted to derive a multi-variate regression equation. With the accumulated data on onset time—a set of quantitative values described above, multi-variate regression can be conducted on the relationship between onset time and a set of quantitative values. In result, a multi-variate regression equation (which is visualized in 400 of FIG. 7) can be prepared for having a set of quantitative values correspond to an onset time.

For instance, the multi-variate regression equation is defined as follows:

$$\text{Onset time}=f(V_I, V_{IL}, V_P, V_{PL}, M, DI_{DWI}, DI_{ADC}, DI_{FLAIR}, DI_{T1}, DI_{T2}, \ldots)$$

Multi-variate regression is a technique that expresses an independent variable through a linear combination of a number of dependent variables, allowing to create a reference variable for classification through the linear combination of a number of quantitative values. However, if there are so many quantitative values, this technique is not effective for creating a reference variable. While multi-variate regression expresses an independent variable through a linear combination of dependent variables, curve fitting is a technique that expresses an independent variable through a second-order or higher-order equation.

A SVM is used to find a hyperplane farthest from a given data, among hyperplanes that separate the data. The SVM performs classification by finding, out of all data, the data that is practically responsible for separating two classes called support vectors. Using these support vectors, the SVM constructs a hyperplane. Since the SVM finds a maximum margin separating hyperplane among all candidate planes, it demonstrates a high performance level.

A decision tree uses a tree-like model of decisions with equality or inequality signs for classification. For instance, suppose that there is A indicating that b is equal to or greater than 5, and B indicating that b is equal to or less than 5. They are each expressed in a decision tree model, and a new input is classified using such a tree. Here, the decision trees should be built optimally for training data, and classification is conducted through this process. Unfortunately though, it is not easy to find an optimal decision tree.

A Bayesian classifier performs classification by extracting posterior information using prior information and likelihood information. It is a technology based on Bayes' Theorem to perform classification on a strongly independent data set among quantitative values. Nevertheless, the SVM is considered to be a more advanced form than the Bayesian classifier.

Figure 8:
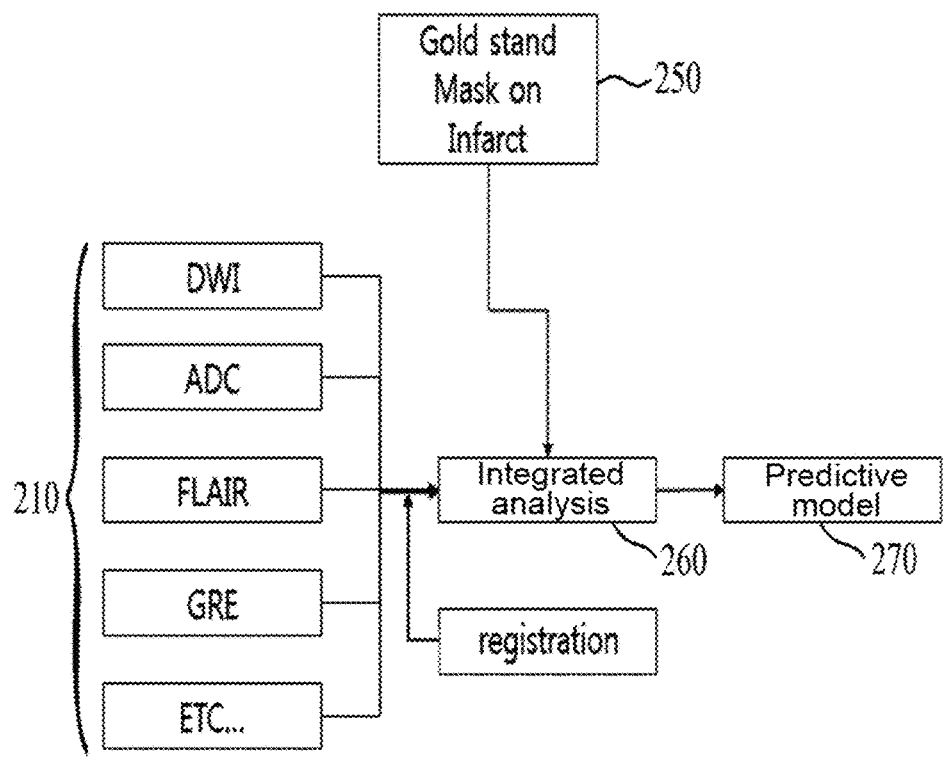
FIG. 8 illustrates an exemplary process for generating a predictive model (corresponding relation) which is used in a method for estimating an onset time of an infarct region based on brain images according to the present disclosure.

FIG. 8 illustrates an exemplary process for generating a predictive model (corresponding relation) which is used in a method for estimating an onset time of an infarct region based on brain images according to the present disclosure. DWI, ADC, FLAIR and GRE images of the brain are obtained and registered to acquire a set of quantitative values (210). This can be done by applying the methods described in FIG. 1 to FIG. 3. An infarct region may be segmented from a DWI image by various ways. For instance, histogram matching or thresholding may be conducted, or an ADC map can be created from the DWI image.

A set of quantitative values is acquired from a number of patients, and an integrated analysis is carried out on a corresponding relation between the set of quantitative values and an onset time of an infarct region (260). For this integrated analysis, a gold stand mask may be used on an infarct (e.g., a neurologist determines an infarct region) (250). For instance, patient's data is acquired from DWI b0, b1000, and a gold standard is produced. This gold standard may be used as a verification standard. A predictive model of integrated analysis results can be created (270).

FIG. 9 illustrates an exemplary data sheet obtained from patients, including dates of data acquisition, whether thrombolysis needs to be performed, image acquisition time from an onset time of an infarct region, and so on. In this manner, it is possible to accumulate data from a greater number of patients.

Figure 10A:
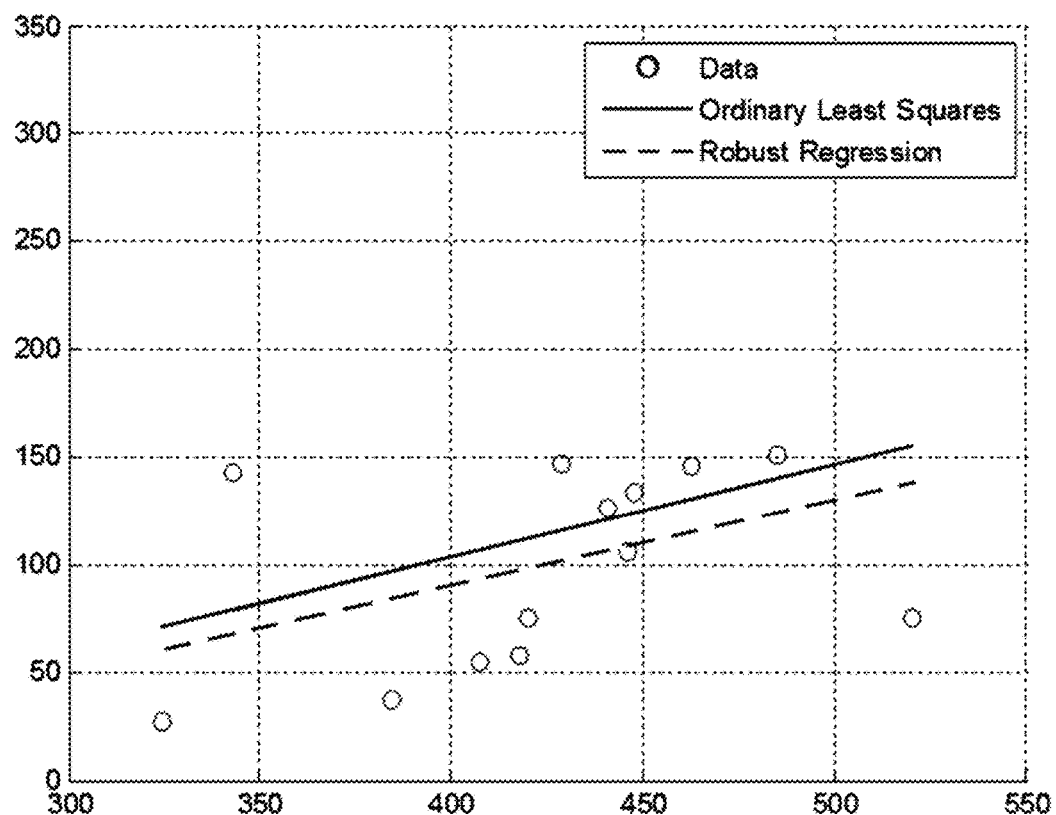
FIGS. 10A and 10B illustrates an exemplary method of robust regression to find the relationship between a set of quantitative values acquired from b0 and b1000 images and an onset time of an infarct region.
Figure 10B:
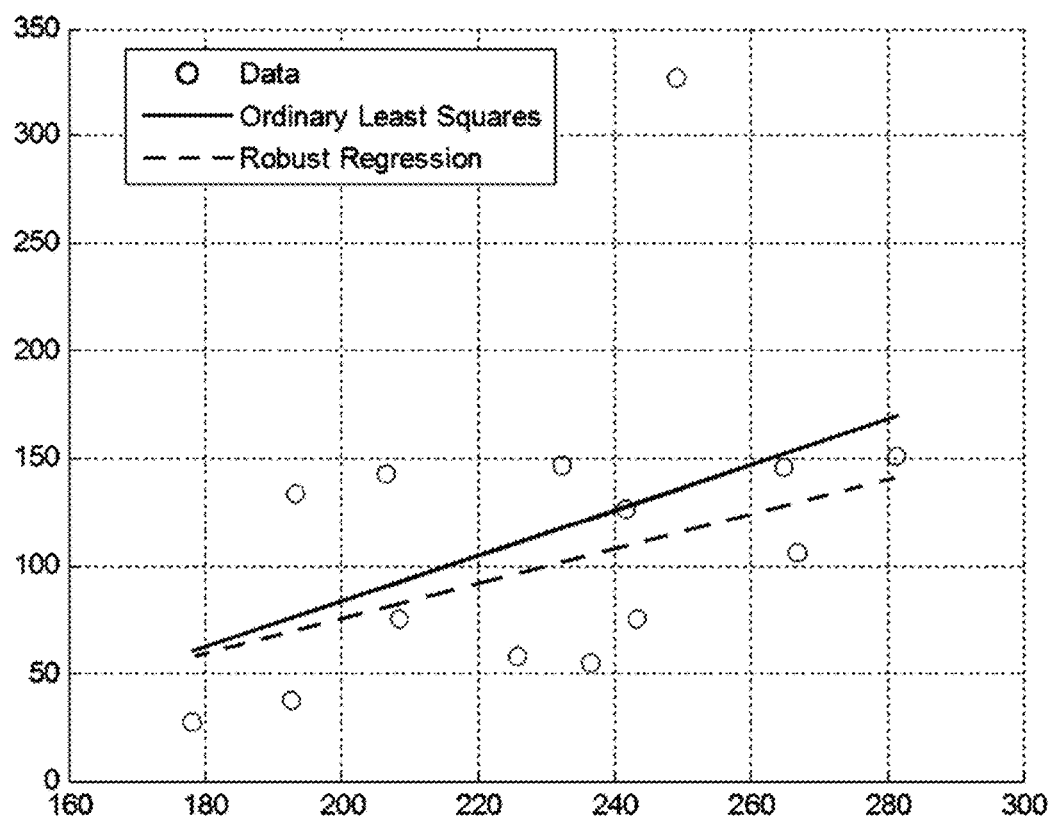

FIG. 10 illustrates an exemplary method of regression to find the relationship between a set of quantitative values acquired from b0 and b1000 images and an onset time of an infarct region. In this drawing, the transverse axis denotes density in an image, and the vertical axis denotes onset time. As shown in FIG. 10, making a prediction using a regression method relatively well represents a real data trend.

Figure 11A:
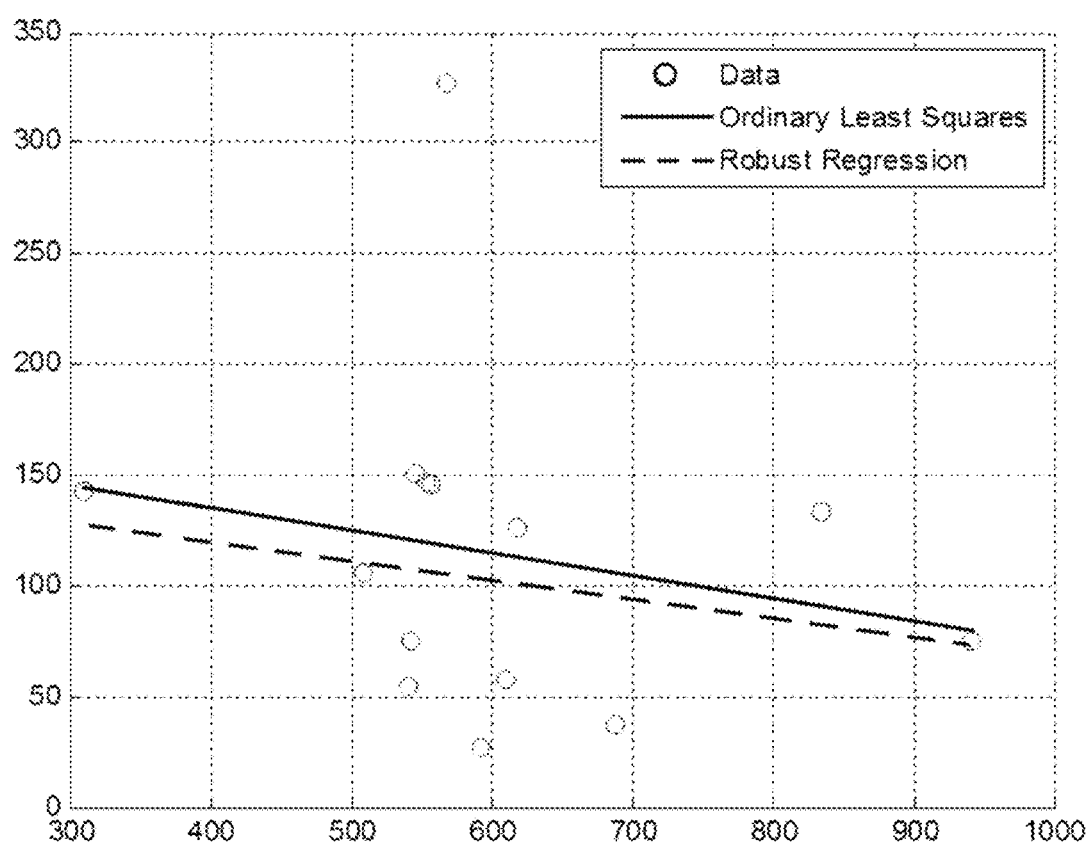
FIGS. 11A and 11B illustrates an exemplary method of robust regression to find the relationship between a set of quantitative values acquired from ADC and FLAIR images and an onset time of an infarct region.
Figure 11B:
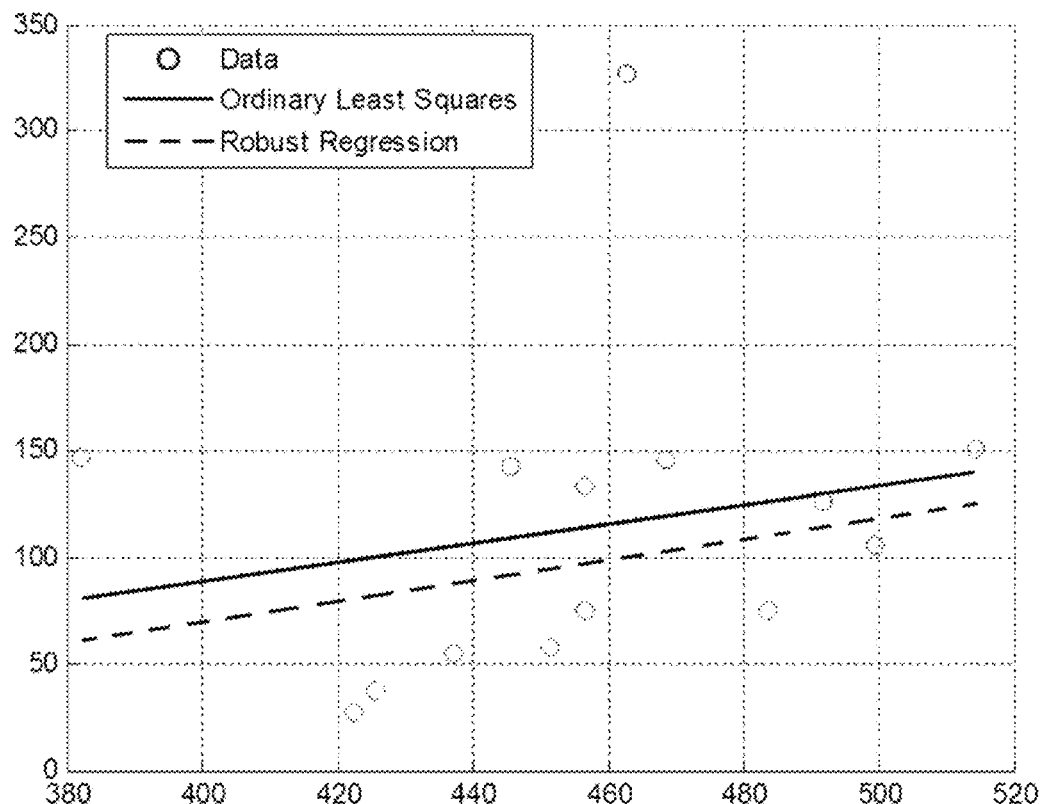

FIG. 11 illustrates an exemplary method of robust regression to find the relationship between a set of quantitative values acquired from ADC and FLAIR images and an onset time of an infarct region. As shown in FIG. 11, making a prediction using a regression method relatively well represents a real data trend.

Figure 12A:
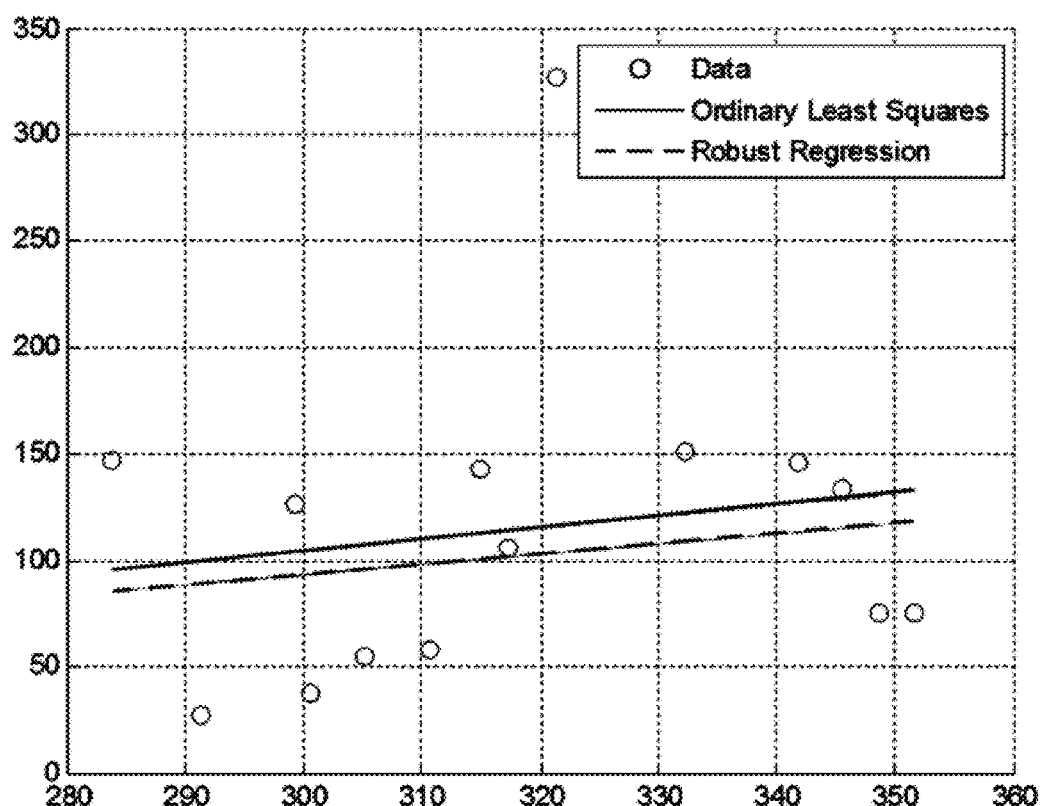

FIG. 12a illustrates an exemplary method of robust regression to find the relationship between a set of quantitative values acquired from GRE images and an onset time of an infarct region, and FIG. 12b illustrates an exemplary method of multi-regression to find the relationship between a set of quantitative values and an onset time of an infarct region. As shown in FIG. 12, making a prediction using a regression method relatively well represents a real data trend.

Figure 13A:
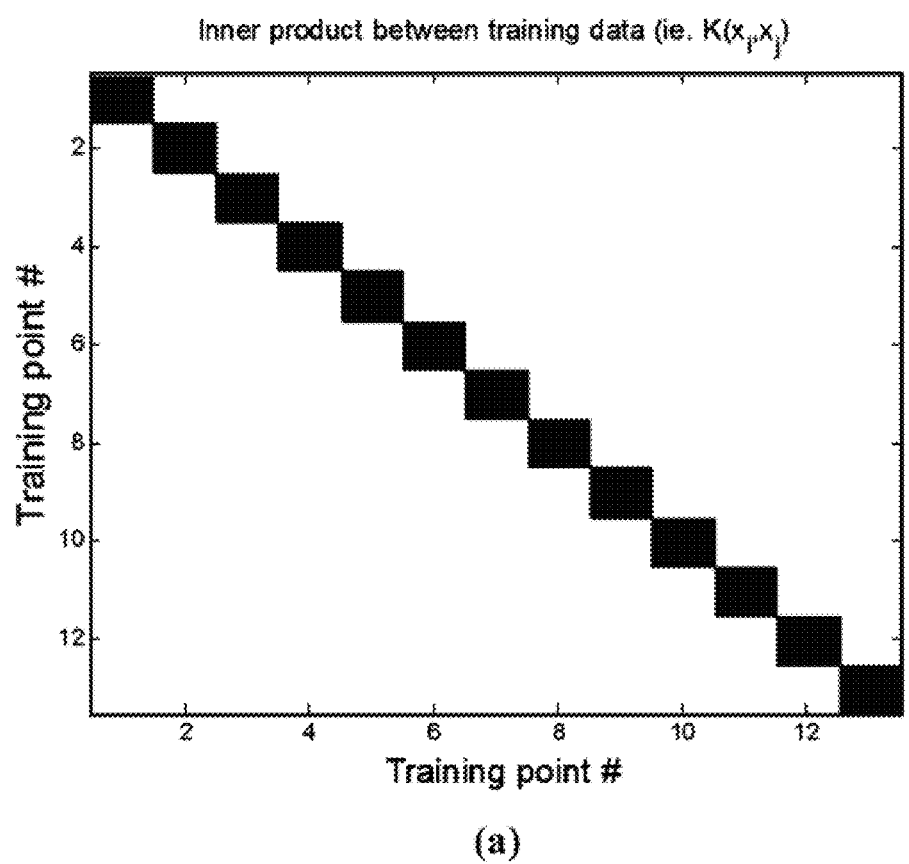
FIGS. 13A and 13B illustrates an exemplary method of support vector regression to find the relationship between a set of quantitative values and an onset time of an infarct region.
Figure 13B:
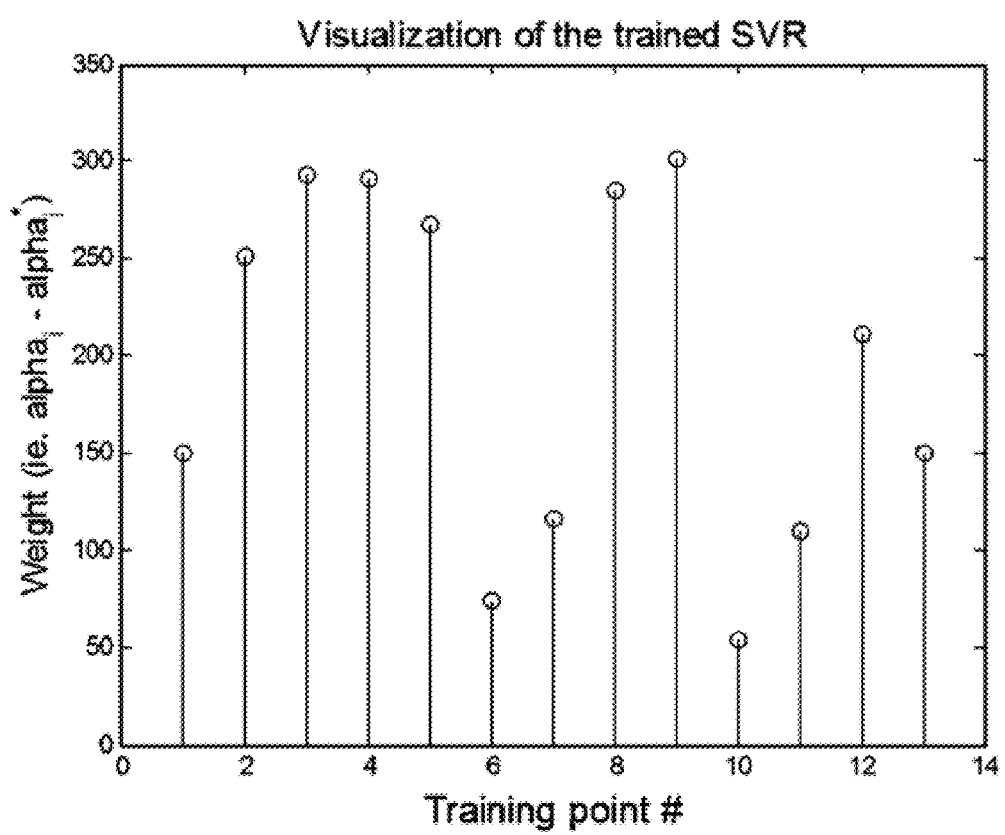

FIG. 13 illustrates an exemplary method of support vector regression to find the relationship between a set of quantitative values and an onset time of an infarct region. In particular, training points and weights are given.

Figure 14:
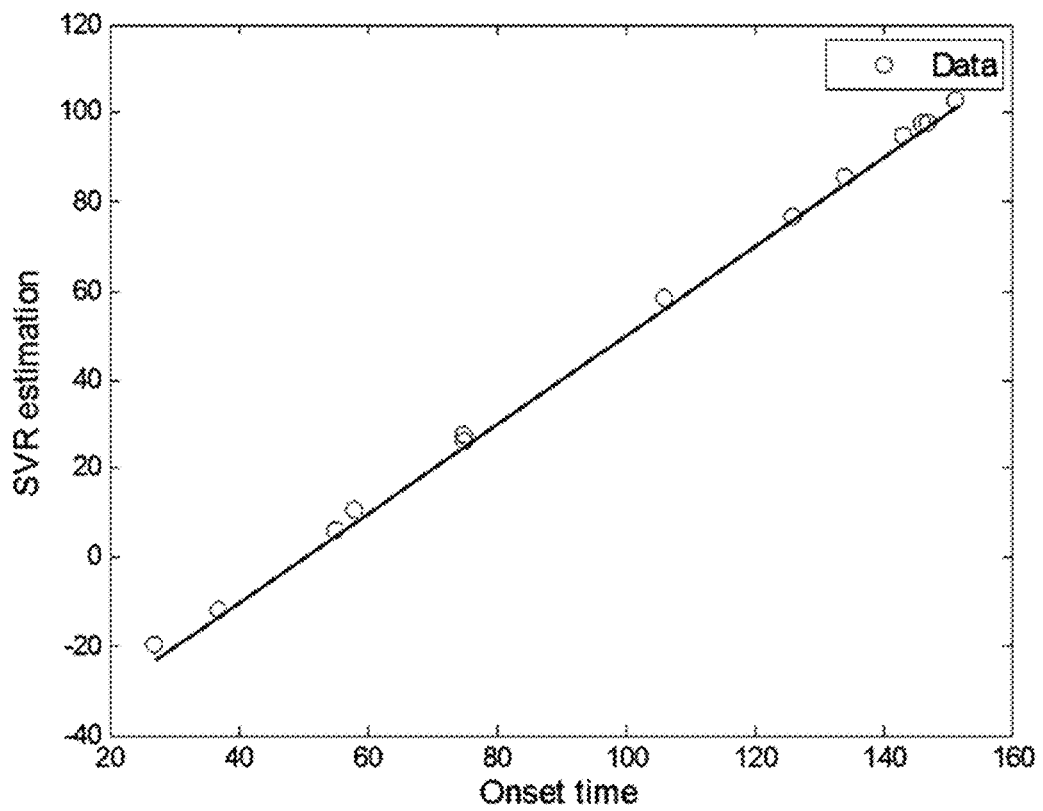
FIG. 14 illustrates the relationship between an onset time of an infarct region obtained from accumulated data and an onset time of an infarct region estimated by an SVR method.

FIG. 14 illustrates the relationship between an onset time of an infarct region obtained from accumulated data and an onset time of an infarct region estimated by an SVR method. Based on this relationship, it is possible to estimate an onset time of an infarct region at a very high accuracy level. The methods for estimating an onset time of an infarct region based on brain images as illustrated in FIG. 9 to FIG. 14 show a statistical trend (regression; p-value of the model >0.05), and the SVR method allows very accurate prediction of an onset time. The accuracy level can be improved even more by conducting more training and testing.

The method for estimating an onset time of an infarct region based on brain images disclosed herein may be performed automatically by an application customized for each process, or performed together with a user interface.

The following will now describe various embodiments of the present disclosure.

A method for estimating an onset time of an infarct region based on brain images, the method comprising: obtaining brain images; extracting from the infarct region included in the brain images a set of quantitative values that vary according to the onset time of the infarct region; and having the set of quantitative values correspond to the onset time of the infarct region by applying a corresponding relation prepared therefor.

The method for estimating an onset time of an infarct region based on brain images can be used to estimate time related a lesion or tissue such as an infarct. The time related to the lesion or tissue includes the time spent on status change, the onset time of a cause of the lesion occurrence and so on.

The method for estimating an onset time of an infarct region based on brain images is applicable to both a human being and an animal.

A method for estimating an onset time of an infarct region based on brain images, wherein the corresponding relation is prepared using a classifier that classifies the set of quantitative values by an onset time of an infarct region.

A method for estimating an onset time of an infarct region based on brain images, further comprising: after obtaining the brain images and before extracting the set of quantitative values, segmenting the infarct region using at least one of the obtained brain images; segmenting a penumbra region of the infarct region using at least one of the obtained brain images; and registering the brain images including the at least one brain images having a segmented infarct or penumbra region.

A method for estimating an onset time of an infarct region based on brain images, wherein the corresponding relation is prepared using a classifier to have a set of accumulated quantitative values acquired from brain images whose onset times of an infarct region are known correspond to an onset time of an infarct region, with the classifier comprising at least one of the following: uni-variate regression, multi-variate regression, robust regression, support vector regression, a decision tree, a Bayesian classifier and curve fitting.

A method for estimating an onset time of an infarct region based on brain images, wherein extracting a set of quantitative values comprises: extracting from the registered brain images at least one information selected from the group consisting of size, location and intensity of the penumbra or infarct region.

The set of quantitative values may include some non-quantitative values. The set of quantitative values may include other features (for example, the shape of the infarct region) as well as the size, location and intensity of the penumbra or infarct region.

A method for estimating an onset time of an infarct region based on brain images, wherein having the set of quantitative values correspond to the onset time of the infarct region comprises: having a set of quantitative values extracted from brain images with an unknown onset time of an infarct region correspond to the onset time of the infarct region by applying the corresponding relation, and revising a corresponding relation using data accumulated by having a set of quantitative values with an unknown onset time of an infarct region correspond to the onset time of the infarct region.

A method for estimating an onset time of an infarct region based on brain images, wherein obtaining the brain images comprises: generating at least two images selected from the group consisting of an MRI-based DWI image, an ADC image, a PWI image, a FLAIR image, a T1 image, a T2 image and a GRE image.

Obtaining the brain images can include a step of acquiring some brain images with different modalities by MRI and a step of acquiring at least one brain image by CT.

A method for estimating an onset time of an infarct region based on brain images, further comprising: after obtaining the brain images and before extracting the set of quantitative values, segmenting the infarct region using the DWI or ADC image; segmenting a penumbra region of the infarct region using the PWI image; and registering the brain images that include the DWI or ADC image with the segmented infarct region or the image with the segmented penumbra region.

A method for estimating an onset time of an infarct region based on brain images, wherein extracting the set of quantitative values comprises: acquiring from the registered brain images two or more quantitative values selected from the group consisting of an infarct volume $V_I$, an infarct location $V_{IL}$, a penumbra volume $V_P$, a penumbra position $V_{PL}$, mismatch M between an infarct region and a penumbra region, an average intensity of the infarct region in each brain image ($DI_{DWT}$, $DI_{ADC}$, $DI_{FLAIR}$, $DI_{T1}$, $DI_{T2}$), and an average intensity of the penumbra region in each brain image ($DP_{DWT}$, $DP_{ADC}$, $DP_{FLAIR}$, $DP_{T1}$, $DP_{T2}$).

A method for estimating an onset time of an infarct region based on brain images, wherein having the set of quantitative values correspond to the onset time of the infarct region comprises: a process in which the onset time of the infarct region corresponds to a first zone for one quantitative value included in the set of the quantitative values; a process in which in which the onset time of the infarct region corresponds to a second zone for another quantitative value included in the set of the quantitative values; and a process in which an intersection of the first and second zones is obtained to narrow down a corresponding zone at the onset time of the infarct region.

A method for estimating an onset time of an infarct region according to the present disclosure allows more accurate and more reasonable estimation of an onset time of a lesion, using quantitative multiple parameters based on brain images.

The invention claimed is:

1. A method for estimating an onset time of an infarct region based on brain images, the method comprising:
    obtaining brain images;
    extracting from the infarct region included in the brain images a set of quantitative values that vary according to the onset time of the infarct region; and
    having the set of quantitative values correspond to the onset time of the infarct region by applying a corresponding relation prepared therefor,
    wherein the corresponding relation is prepared using a classifier that classifies the set of quantitative values by the onset time of the infarct region.

2. The method according to claim 1, further comprising:
    after obtaining the brain images and before extracting the set of quantitative values, segmenting the infarct region using at least one of the obtained brain images;
    segmenting a penumbra region of the infarct region using at least one of the obtained brain images; and registering the brain images including the at least one brain images having a segmented infarct or penumbra region.

3. The method according to claim 2, wherein extracting the set of quantitative values comprises:
extracting from the registered brain images at least one information selected from the group consisting of size, location and intensity of the penumbra or infarct region.

4. The method according to claim 1, wherein the corresponding relation is prepared using the classifier to have a set of accumulated quantitative values acquired from brain images whose onset times of the infarct region are known correspond to the onset time of the infarct region, with the classifier comprising at least one of the following: uni-variate regression, multi-variate regression, robust regression, support vector regression, a decision tree, a Bayesian classifier and curve fitting.

5. The method according to claim 4, wherein having the set of quantitative values correspond to the onset time of the infarct region comprises:
having the set of quantitative values extracted from brain images with an unknown onset time of the infarct region correspond to the onset time of the infarct region by applying the corresponding relation, and
revising the corresponding relation using data accumulated by having the set of quantitative values with the unknown onset time of the infarct region correspond to the onset time of the infarct region.

6. The method according to claim 1, wherein obtaining the brain images comprises:
generating at least two images selected from the group consisting of an MRI-based DWI image, an ADC image, a PWI image, a FLAIR image, a T1 image, a T2 image and a GRE image.

7. The method according to claim 6, further comprising:
after obtaining the brain images and before extracting the set of quantitative values, segmenting the infarct region using the DWI or ADC image;
segmenting a penumbra region of the infarct region using the PWI image; and
registering the brain images that include the DWI or ADC image with the segmented infarct region or the PWI image with the segmented penumbra region.

8. The method according to claim 7, wherein extracting the set of quantitative values comprises:
acquiring from the registered brain images two or more quantitative values selected from the group consisting of an infarct volume $V_I$, an infarct location $V_{IL}$, a penumbra volume $V_P$, a penumbra position $V_{PL}$, mismatch M between the infarct region and the penumbra region, an average intensity of the infarct region in a respective brain image, and an average intensity of the penumbra region in the respective brain image.

9. The method according to claim 1, wherein having the set of quantitative values correspond to the onset time of the infarct region comprises:
a process in which the onset time of the infarct region corresponds to a first zone for one quantitative value included in the set of the quantitative values;
a process in which in which the onset time of the infarct region corresponds to a second zone for another quantitative value included in the set of the quantitative values; and
a process in which an intersection of the first and second zones is obtained to narrow down a corresponding zone at the onset time of the infarct region.

* * * * *